US011352428B2

(12) United States Patent
Ware et al.

(10) Patent No.: US 11,352,428 B2
(45) Date of Patent: Jun. 7, 2022

(54) MODULATION OF IMMUNE RESPONSE USING BTLA AGONIST ANTIBODIES

(71) Applicant: Sanford Burnham Prebys Medical Discovery Institute, La Jolla, CA (US)

(72) Inventors: Carl F. Ware, La Jolla, CA (US); John Sedy, La Jolla, CA (US); Paula Norris, La Jolla, CA (US)

(73) Assignee: Sanford Burnham Prebys Medical Discovery Institute, La Jolla, CA (US)

( * ) Notice: Subject to any disclaimer, the term of this patent is extended or adjusted under 35 U.S.C. 154(b) by 111 days.

(21) Appl. No.: 15/570,013

(22) PCT Filed: Apr. 29, 2016

(86) PCT No.: PCT/US2016/030138
§ 371 (c)(1),
(2) Date: Oct. 27, 2017

(87) PCT Pub. No.: WO2016/176583
PCT Pub. Date: Nov. 3, 2016

(65) Prior Publication Data
US 2018/0155426 A1 Jun. 7, 2018

Related U.S. Application Data

(60) Provisional application No. 62/154,484, filed on Apr. 29, 2015.

(51) Int. Cl.
| | | |
|---|---|---|
| *C07K 16/28* | (2006.01) | |
| *A61P 37/00* | (2006.01) | |
| *A61P 29/00* | (2006.01) | |
| *C07K 14/715* | (2006.01) | |
| *A61K 39/00* | (2006.01) | |

(52) U.S. Cl.
CPC .......... *C07K 16/2818* (2013.01); *A61P 29/00* (2018.01); *A61P 37/00* (2018.01); *C07K 14/7151* (2013.01); *A61K 2039/505* (2013.01); *C07K 2317/34* (2013.01); *C07K 2317/75* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 8,349,320 B2 * | 1/2013 | Ware .................... | A61K 38/177 424/130.1 |
| 8,563,694 B2 | 10/2013 | Mataraza et al. | |
| 2006/0204498 A1* | 9/2006 | Proudfoot ................. | A61P 9/00 424/145.1 |
| 2009/0239799 A1* | 9/2009 | Flaishon .............. | A61K 38/195 514/1.1 |
| 2012/0183565 A1 | 7/2012 | Mataraza et al. | |
| 2014/0220051 A1 | 8/2014 | Ware et al. | |

FOREIGN PATENT DOCUMENTS

| | | |
|---|---|---|
| WO | WO 2011/014438 A1 | 2/2011 |
| WO | WO 2014/183885 A1 | 11/2014 |
| WO | WO 2015/035063 A2 | 3/2015 |
| WO | WO-2016176583 A1 | 11/2016 |

OTHER PUBLICATIONS

Lejeune et al., 2006, Canc. Immunity vol. 6: 1-17 Chevalier et al., 2013, Blood. Vol. 121: 29-37.*
Cheung et al., 2009, J. Immunol. vol. 183: 7286-7296.*
Mor et al., 2005, J. Immunol. vol. 175: 3439-3445.*
Whisstock et al., 2003, Quart. Rev. Biophys. vol. 36: 307-340.*
Sheibanie et al., 2007, Arht. Rheum. vol. 56: 2608-2619.*
WInkler et al., 2000, J. Immunol. vol. 165: 4505-14.*
Chen et al., 1992, J. Exp. Med. vol. 176: 855-66.*
Vajdos et al., 2002, J. Mol. Biol. vol. 320: 415-428.*
Klimka et al., Brit. J. Cancer. 2000: 252-260.*
Dondelinger et al., 2018: Front. Immunol. vol. 1-15.*
Bekiaris, Vasileios et al.: "*The Inhibitory Receptor BTLA Controls [gamma][delta] T Cell Homeostasis and Inflammatory Responses*"; Immunity, Dec. 5, 2013, vol. 39, No. 6, 31 pgs, XP055361147.
Extended European Search Report dated Aug. 13, 2018, regarding ep 16 787 238.1.
PCT/US2016/030138 International Search Report and Written Opinion dated Oct. 7, 2016.

* cited by examiner

*Primary Examiner* — Amy E Juedes
(74) *Attorney, Agent, or Firm* — McNeill Baur PLLC

(57) ABSTRACT

The present invention relates to the seminal discovery that BTLA agonist antibodies modulate the immune system. Specifically, the present invention provides antibodies which bind BTLA in the activated state enhancing BTLA signaling. The present invention further provides methods of treating immune and inflammatory diseases and disorders with a BTLA agonist antibody.

7 Claims, 9 Drawing Sheets

Specification includes a Sequence Listing.

Light Chain

```
  1 DIQMTQSPSV LSVSVGDRVT LNCKASHNIK NYLNWYQQKL
    GEAPKLLIYD
 51 TVNLQTGIPS RFSGSGSGTD FTVTISSLQP EDVATYFCFQ
    YHSWPYTFGA
101 GTKLELKRAD AAPTVSIFPP SMEQLTSGGA
    TVVCFVNNFY
    PRDISVKWKI 151 DGSEQRDGVL DSVTDQDSKD
    STYSMSSTLS LTKVEYERHN LYTCEVVHKT 201 SSSPVVKSFN RNEC
```

FIG. 3A

Heavy Chain

```
  1 EVQILETGGG LVKPGGSLRL SCATSGFNFN DYFVNWVRQA
    PGKGLQWVAQ
 51 IRNKNYNPAT YYAESLEGRV TISRDDSKSS VYLQVSSVRA
    EDTAIYCSP 101 ISSYYHDGSL HYSDYWGQGV MVTVSSAETT
    APSVYPLAPG TALKSNSMVT 151 LGCLVKGYFP EPVTVTWNSG
    ALSSGVHTFP AVLQSGLYTL TSSVTVPSST 201 WPSQTVTCNV
    AHPASSTKVD KKIVPRNCGG DCKPCICTGS EVSSVFIFPP 251
    KPKDVLTITL TPKVTCVVVD ISQDDPEVHF SWFVDDVEVH TAQTRPPEEQ
301 FNSTFRSVSE LPILHQDWLN GRTFERCKVTS AAFPSPIEKT
    ISKPEGRTQV 351 PHVYTMSPTK EEMLQNEVSI TCMVKGFYPP
    DIYVEWQMNG QPQENYKNTP 401 PTMDTDGSYF LYSKLNVKKE
    KWQQGNTFTC SVLHEGLHNH HTEKSLSHSP 451 GK
```

FIG. 3B

MODULATION OF IMMUNE RESPONSE USING BTLA AGONIST ANTIBODIES

CROSS-REFERENCE TO RELATED APPLICATIONS

This application is a 35 USC § 371 National Stage application of International Application No. PCT/US2016/030138 filed Apr. 29, 2016; which claims the benefit under 35 USC § 119(e) to U.S. Application Ser. No. 62/154,484 filed Apr. 29, 2015. The disclosure of each of the prior applications is considered part of and is incorporated by reference in the disclosure of this application.

STATEMENT OF GOVERNMENT SUPPORT

This invention was made in part with government support under Grant No. R37AI033068 awarded by the National Institutes of Health. The United States government has certain rights in this invention.

INCORPORATION OF SEQUENCE LISTING

The material in the accompanying sequence listing is hereby incorporated by reference into this application. The accompanying sequence listing text file, name BURN1660_1WO_Sequence_Listing, was created on Apr. 28, 2016, and is 7 kb. The file can be assessed using Microsoft Word on a computer that uses Windows OS.

FIELD OF THE INVENTION

The present invention relates to generally to antibodies and more specifically to the development and of use of BTLA agonist antibodies and uses thereof to modulate immune response and treat immune and inflammatory related diseases and disorders.

BACKGROUND OF THE INVENTION

Lymphocyte activation involves signals delivered through primary antigen receptors-either the T-cell receptor or B-cell receptor—as well as secondary signals delivered through an array of co-stimulatory and inhibitory receptors that regulate the extent, quality and duration of lymphocyte activation. For T cells, the co-stimulatory receptor and inhibitory cell surface receptors include CD28, cytotoxic T-lymphocyte antigen 4 (CTLA-4), and several members of the tumor necrosis factor (TNF) receptor (TNFR) family. The co-stimulatory receptors of the immunoglobulin superfamily include CD28 and inducible T-cell co-stimulator (ICOS), and the inhibitory receptors include CTLA-4, and programmed cell death 1 (PD-1) and B and T cell lymphocyte attenuator (BTLA). The CD28 family of receptors consisting of CD28, ICOS, CTLA-4, PD-1 and B and T lymphocyte attenuator (BTLA) play a prominent role in regulating the initiation of an immune response. Ligation of either CD28 or ICOS enhances T cell activation whereas engagement of CTLA-4, PD-1 or BTLA attenuates the T cell response.

There is a large unmet need for novel therapies designed to inhibit lymphocyte activity in patients suffering from immune mediated pathology such as in graft versus host disease or autoimmune diseases. In many types of these diseases there is a limited array of approved treatments, or some individuals fail to respond to available treatments. An attractive target for novel therapies is agonistic activation of inhibitory receptors expressed by pathogenic lymphocytes that are the cause of autoimmune disease. Attempts to develop antibody-based therapy designed to activate human inhibitory receptors have largely met with failure despite promising results in animal models.

SUMMARY OF THE INVENTION

The present invention relates to the seminal discovery that BTLA agonist antibodies modulate an immune response. Specifically, the present invention provides antibodies that bind BTLA in the activated state enhancing BTLA signaling. The present invention further provides methods of treating immune and inflammatory diseases and disorders with a BTLA agonist antibody as described herein.

In one embodiment, the present invention provides a method of treating an autoimmune or inflammatory disorder comprising administering a therapeutic agent that modulates the activity of BTLA to a subject in need thereof, thereby treating the autoimmune or inflammatory disorder. In one aspect, the autoimmune or inflammatory disorder is Addison's disease, amyotrophic lateral sclerosis, Crohn's disease, Cushing's Syndrome, diabetes mellitus type 1, graft versus host disease, Graves' disease, Guillain-Barré syndrome, lupus erythematosus, multiple sclerosis, psoriasis, psoriatic arthritis, rheumatoid arthritis, sarcoidosis, scleroderma, systemic lupus erythematosus, cancer, transplant rejection, or vasculitis. In one preferred aspect, the therapeutic agent is an antibody. In another aspect, the antibody binds to BTLA. In a further aspect, the antibody is an agonistic antibody. In an additional aspect, the antibody binds activated BTLA. In certain aspects, the antibody does not block HVEM binding to BTLA. In one aspect, BTLA signaling is enhanced. In another aspect, the antibody is monoclonal, chimeric, human or humanized or binding fragments thereof. In a specific aspect, the agonistic clone of the antibody is 6F4 as described herein.

In an additional aspect, an immune response modulator is administered. In certain aspects, the immune response modulator is an eicosanoid, cytokine, prostaglandin, interleukin, chemokine or interferon. In a further aspect, the immune response modulators is CXCL-8, CCL2, CCL3, CCL4, CCL5, CCL11, CXCL10, IL1, IL2, IL3, IL4, IL5, IL6, IL7, IL8, IL9, IL10, IL11, IL12, IL13, IL15, IL17, IL17, INF-α, INF-β, INF-ε, INF-γ, G-CSF, TNF-α, CTLA, CD20, or CD52. In a specific aspect, the immune response modulator is for example, but not limited to, tocilizumab (Actemra), CDP870 (Cimzia), enteracept (Enbrel), adalimumab (Humira), Kineret, abatacept (Orencia), infliximab (Remicade), rituzimab (Rituxan), golimumab (Simponi), Avonex, Rebif, ReciGen, Plegridy, Betaseron, Copaxone, Novatrone, natalizumab (Tysabri), fingolimod (Gilenya), teriflunomide (Aubagio), BG12, Tecfidera, or alemtuzumab (Campath, Lemtrada).

In another embodiment, the present invention provides a method of decreasing T cell activity comprising contacting a T cell with an agent that modulates the activity of BTLA. In one aspect, the therapeutic agent is an anti-BTLA agonistic antibody. In another aspect, the antibody binds activated BTLA. In an additional aspect, the antibody does not block HVEM binding to BTLA. In a certain aspects, the antibody enhances BTLA signaling. In a specific aspect, the antibody clone is 6F4. The contacting can be in vivo or ex vivo for example.

In an additional embodiment, the present invention provides an antibody that binds activated BTLA. In one aspect, the antibody does not block HVEM binding to BTLA. In another aspect, BTLA signaling is enhanced. In an additional aspect, the binding of the antibody to BTLA results in phosphorylation of the cytoplasmic domain of BTLA. In a further aspect, the binding of the antibody to BTLA recruits SHP1 and SHP2. In a specific aspect, the antibody clone is 6F4.

In a further embodiment, the present invention provides a pharmaceutical composition comprising an anti-BTLA antibody and a pharmaceutically acceptable carrier.

In one embodiment, the present invention provides a method of screening for a BTLA agonist agent comprising contacting the agent with BTLA; and measuring BTLA activity, wherein an increase in BTLA activity indicates that the agent is a BTLA agonist. In one aspect, the agent is an antibody, antibody fragment or a peptide. In an additional aspect, the antibody is monoclonal, chimeric, human or humanized. In a further aspect, the antibody binds to the same epitope as clone 6F4.

BRIEF DESCRIPTION OF THE DRAWINGS

FIGS. 3A-3B show the protein sequence of rat anti-hBLTA Mab Clone 6F4. Amino acid sequence for (A) the light chain and (B) the heavy chain of rat anti-hBLTA Mab Clone 6F.

DETAILED DESCRIPTION OF THE INVENTION

Figure 1A:
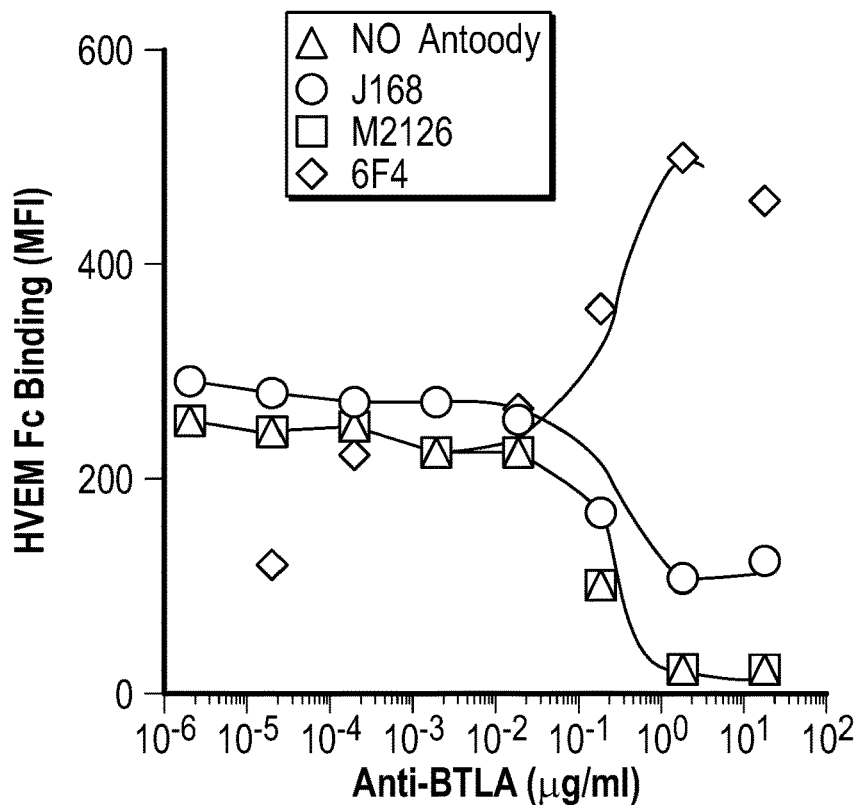
FIGS. 1A-1C show characterization of anti-BTLA monoclonal antibodies. BJAB cells transduced with BTLA were incubated with the indicated concentrations of anti-BTLA prior to staining with HVEM-Fc (A) or human CMV UL144-Fc (B). (C). Two images of BTLA are shown.

The present invention relates to the seminal discovery that BTLA agonist antibodies modulate the immune system and immune responses. Specifically, the present invention provides antibodies that bind BTLA in the activated state enhancing BTLA signaling. The present invention further provides methods of treating immune and inflammatory diseases and disorders with a BTLA agonist antibody.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. The definitions set forth below are for understanding of the disclosure but shall in no way be considered to supplant the understanding of the terms held by those of ordinary skill in the art.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains. Each variable region is comprised of three segments called complementarity-determining regions (CDRs) or hypervariable regions and a more highly conserved portions of variable domains are called the framework region (FR). The variable domains of heavy and light chains each comprise four FR regions, largely adopting a β-sheet configuration, connected by three CDRs, which form loops connecting, and in some cases forming part of the β-sheet structure. The CDRs in each chain are held together in close proximity by the FRs and, with the CDRs from the other chain, contribute to the formation of the antigen-binding site of antibodies. The constant domains are not involved directly in binding an antibody to an antigen, but exhibit various effector functions, such as participation of the antibody in antibody dependent cellular cytotoxicity.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called α, δ, ε, γ, and μ, respectively. The subunit structures and three-dimensional configurations of different classes of immunoglobulins are well known.

The term "antibody" as used herein refers to intact monoclonal antibodies, polyclonal antibodies, multispecific antibodies (e.g. bispecific antibodies) formed from at least two intact antibodies, and antibody fragments so long as they exhibit the desired biological activity.

"Antibody fragments" comprise a portion of an intact antibody, preferably the antigen binding or variable region of the intact antibody. Examples of antibody fragments include Fab, Fab', F(ab')$_2$, and Fv fragments; diabodies, tribodies and the like; linear antibodies; single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore each monoclonal antibody is directed against a single determinant on the antigen. In addition to their specificity, the monoclonal antibodies are advantageous in that they are synthesized by the hybridoma culture, uncontaminated by other immunoglobulins. For example, the monoclonal antibodies to be used in accordance with the present invention may be made by hybridomas, by recombinant DNA methods or isolated from phage antibody libraries.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

"Humanized" forms of non-human (e.g., murine) antibodies are chimeric immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. For the most part, humanized antibodies are human immunoglobulins (recipient antibody) in which residues from a complementarity determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDRs correspond to those of a non-human immunoglobulin and all or substantially all of the FRs are those of a human immunoglobulin sequence. The humanized antibody optimally also will comprise at least a portion of an immunoglobulin constant region (Fc), typically that of a human immunoglobulin.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding.

As used herein, the terms "treating" or "treatment" or "alleviation" refer to therapeutic treatment, prophylactic and/or preventative measures, wherein the object is to prevent or slow down (lessen) the targeted pathologic condition or disorder. Those in need of treatment include those already with the disorder as well as those prone to have the disorder or those in whom the disorder is to be prevented.

The term "therapeutic agent" as used herein includes a chemical compound or composition capable of inducing a desired therapeutic effect when administered to a patient or subject. An example of a therapeutic agent of the present invention is an anti-BTLA antibody.

As used herein, the terms "effective amount" or "therapeutically effective amount" of a drug used to treat a disease is an amount that can reduce the severity of a disease, reduce the severity of one or more symptoms associated with the disease or its treatment, or delay the onset of more serious symptoms or a more serious disease that can occur with some frequency following the treated condition. An "effective amount" may be determined empirically and in a routine manner, in relation to the stated purpose.

The therapeutic agent may be administered by any suitable means, including topical, parenteral, subcutaneous, intraperitoneal, intrapulmonary, intranasal, intravenous, and/or intralesional administration in order to treat the subject. However, in exemplary embodiments, the therapeutic agent is formulated for topical application, such as in the form of a liquid, cream, gel, ointment, foam spray or the like As used herein the terms "disorder" or "disease" refers to any condition that would benefit from treatment with the anti-BTLA antibody. Examples of diseases and disorders that would benefit from anti-BTLA treatment include immune, autoimmune and inflammatory diseases and disorders.

An immune disease or disorder is a dysfunction of the immune system. These disorders can be characterized in several different ways: by the component(s) of the immune system affected; by whether the immune system is overactive or underactive and by whether the condition is congenital or acquired. Autoimmune diseases arise from an abnormal immune response of the body against substances and tissues normally present in the body (autoimmunity). A major understanding of the underlying pathophysiology of autoimmune diseases has been the application of genome wide association scans that have identified a striking degree of genetic sharing among the autoimmune diseases.

Autoimmune disorders include, but are not limited to, Acute disseminated encephalomyelitis (ADEM), Addison's disease, Agammaglobulinemia, Alopecia areata, Amyotrophic lateral sclerosis (aka Lou Gehrig's disease), Ankylosing Spondylitis, Antiphospholipid syndrome, Antisynthetase syndrome, Atopic allergy, Atopic dermatitis, Autoimmune aplastic anemia, Autoimmune cardiomyopathy, Autoimmune enteropathy, Autoimmune hemolytic anemia, Autoimmune hepatitis, Autoimmune inner ear disease, Autoimmune lymphoproliferative syndrome, Autoimmune pancreatitis, Autoimmune peripheral neuropathy, Autoimmune polyendocrine syndrome, Autoimmune progesterone dermatitis, Autoimmune thrombocytopenic purpura, Autoimmune urticaria, Autoimmune uveitis, Balo disease/Balo concentric sclerosis, Behcet's disease, Berger's disease, Bickerstaffs encephalitis, Blau syndrome, Bullous pemphigoid, Cancer, Castleman's disease, Celiac disease, Chagas disease, Chronic inflammatory demyelinating polyneuropathy, Chronic inflammatory demyelinating polyneuropathy, Chronic obstructive pulmonary disease, Chronic recurrent multifocal osteomyelitis, Churg-Strauss syndrome, Cicatricial pemphigoid, Cogan syndrome, Cold agglutinin disease, Complement component 2 deficiency, Contact dermatitis, Cranial arteritis, CREST syndrome, Crohn's disease, Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Discoid lupus erythematosus, Dressler's syndrome, Drug-induced lupus, Eczema, Endometriosis, Eosinophilic fasciitis, Eosinophilic gastroenteritis, Eosinophilic pneumonia, Epidermolysis bullosa acquisita, Erythema nodosum, Erythroblastosis fetalis, Essential mixed cryoglobulinemia, Evan's syndrome, Fibrodysplasia ossificans progressiva, Fibrosing alveolitis (or Idiopathic pulmonary fibrosis), Gastritis, Gastrointestinal pemphigoid, Glomerulonephritis, Goodpasture's syndrome, graft versus host disease, Graves' disease, Guillain-Barré syndrome, Hashimoto's encephalopathy, Hashimoto's thyroiditis, Henoch-Schonlein purpura, Herpes gestationis aka Gestational Pemphigoid, Hidradenitis suppurativa, Hughes-Stovin syndrome, Hypogammaglobulinemi, Idiopathic inflammatory demyelinating diseases, Idiopathic pulmonary fibrosis, Idiopathic thrombocytopenic purpura, IgA nephropathy, Inclusion body myositis, Interstitial cystitis, Juvenile idiopathic arthritis aka Juvenile rheumatoid arthritis, Kawasaki's disease, Lambert-Eaton myasthenic syndrome, Leukocytoclastic vasculitis, Lichen planus, Lichen sclerosus, Linear IgA disease, Lupoid hepatitis aka Autoimmune hepatitis, Lupus erythematosus, Majeed syndrome, Microscopic colitis, Microscopic polyangiitis, Miller-Fisher syndrome, Mixed connective tissue disease, Morphea, Mucha-Habermann disease aka Pityriasis lichenoides et varioliformis acuta, Multiple sclerosis, Myasthenia gravis, Myositis, Ménière's disease, Narcolepsy, Neuromyelitis optica, Neuromyotonia, Occular cicatricial pemphigoid, Opsoclonus myoclonus syndrome, Ord's thyroiditis, Palindromic rheumatism, PANDAS (pediatric autoimmune neuropsychiatric disorders associated with *streptococcus*), Paraneoplastic cerebellar degeneration, Paroxysmal nocturnal hemoglobinuria (PNH), Parry Romberg syndrome, Pars planitis, Parsonage-Turner syndrome, Pemphigus vulgaris, Perivenous encephalomyelitis, Pernicious anaemia, POEMS syndrome, Polyarteritis nodosa, Polymyalgia rheumatica, Polymyositis, Primary biliary cirrhosis, Primary sclerosing cholangitis, Progressive inflammatory neuropathy, Psoriasis, Psoriatic arthritis, Pure red cell aplasia, Pyoderma gangrenosum, Rasmussen's encephalitis, Raynaud phenomenon, Reiter's syndrome, Relapsing polychondritis, Restless leg syndrome, Retroperitoneal fibrosis, Rheumatic fever, Rheumatoid arthritis, Sarcoidosis, Schizophrenia, Schmidt syndrome, Schnitzler syndrome, Scleritis, Scleroderma, Serum Sickness, Sjögren's syndrome, Spondyloarthropathy, Stiff person syndrome, Still's disease, Subacute bacterial endocarditis (SBE), Susac's syndrome, Sweet's syndrome, Sydenham chorea, Sympathetic ophthalmia, Systemic lupus erythematosus, Takayasu's arteritis, Temporal arteritis, Thrombocytopenia, Tolosa-Hunt syndrome, Transverse myelitis, Ulcerative colitis, Undifferentiated spondyloarthropathy, Urticarial vasculitis, Vasculitis, Vitiligo, Wegener's granulomatosis.

Inflammatory disease are a large group of disorders that underlie a vast variety of human diseases. The immune system is often involved with inflammatory disorders, demonstrated in both allergic reactions and some myopathies, with many immune system disorders resulting in abnormal inflammation. Non-immune diseases with etiological origins in inflammatory processes include cancer, atherosclerosis, and ischaemic heart disease. A large variety of proteins are involved in inflammation, and any one of them is open to a genetic mutation which impairs or otherwise dysregulates the normal function and expression of that protein. Examples of disorders associated with inflammation include Acne vulgaris, Asthma, Autoimmune diseases, Celiac disease, Chronic prostatitis, Glomerulonephritis, Hypersensitivities, Inflammatory bowel diseases, Pelvic inflammatory disease, Reperfusion injury, Rheumatoid arthritis, Sarcoidosis, Transplant rejection, Vasculitis, Interstitial cystitis, Atherosclerosis, Allergies, Myopathies, leukocyte defects and cancer.

The term "immune modulator" as used herein refers to any therapeutic agent that modulates the immune system. Examples of immune modulators include eicosanoids, cytokines, prostaglandins, interleukins, chemokines and interferons. Specific examples of immune modulators include PGI2, PGE2, PGF2, CCL14, CCL19, CCL20, CCL21, CCL25, CCL27, CXCL12, CXCL13, CXCL-8, CCL2, CCL3, CCL4, CCL5, CCL11, CXCL10, IL2, IL3, IL4, IL5, IL6, IL7, IL8, IL9, IL10, IL11, IL12, IL13, IL15, IL17, IL17, INF-α, INF-β, INF-ε, INF-γ, G-CSF, TNF-α, CTLA, CD20, and CD52. Other examples of immune modulators include tocilizumab (Actemra), CDP870 (Cimzia), enteracept (Enbrel), adalimumab (Humira), Kineret, abatacept (Orencia), infliximab (Remicade), rituzimab (Rituxan), golimumab (Simponi), Avonex, Rebif, ReciGen, Plegridy, Betaseron, Copaxone, Novatrone, natalizumab (Tysabri), fingolimod (Gilenya), teriflunomide (Aubagio), BG12, Tecfidera, and alemtuzumab (Campath, Lemtrada).

The immune system is a system of biological structures and processes within an organism that protects against disease. This system is a diffuse, complex network of interacting cells, cell products, and cell-forming tissues that protects the body from pathogens and other foreign substances, destroys infected and malignant cells, and removes cellular debris: the system includes the thymus, spleen, lymph nodes and lymph tissue, stem cells, white blood cells, antibodies, and lymphokines. B cells or B lymphocytes are a type of lymphocyte in the humoral immunity of the adaptive immune system and are important for immune surveillance. T cells or T lymphocytes are a type of lymphocyte that plays a central role in cell-mediated immunity. There are two major subtypes of T cells: the killer T cell and the helper T cell. In addition there are suppressor T cells which have a role in modulating immune response. Killer T cells only recognize antigens coupled to Class I MHC molecules, while helper T cells only recognize antigens coupled to Class II MHC molecules. These two mechanisms of antigen presentation reflect the different roles of the two types of T cell. A third, minor subtype are the γδ T cells that recognize intact antigens that are not bound to MHC receptors. In contrast, the B cell antigen-specific receptor is an antibody molecule on the B cell surface, and recognizes whole pathogens without any need for antigen processing. Each lineage of B cell expresses a different antibody, so the complete set of B cell antigen receptors represent all the antibodies that the body can manufacture B and T cell attenuator (BTLA or CD272) is an integral part of the immune system. BTLA expression is induced during activation of T cells, and BTLA remains expressed on Th1 cells but not Th2 cells. Like programmed cell death 1 (PD1) and cytotoxic T-lymphocyte associate protein 4 (CTLA4), BTLA activates inhibitory pathways, regulating T cell activation. However, unlike PD-1 and CTLA-4, BTLA displays T-cell inhibition via interaction with tumor necrosis family receptors (TNF-R), not the B7 family of cell surface receptors. BTLA is a ligand for tumor necrosis factor (receptor) superfamily, member 14 (TNFRSF14), also known as herpes virus entry mediator (HVEM). BTLA-HVEM complexes negatively regulate T-cell immune responses.

The tumor necrosis factor receptor superfamily member (TNFRSF) herpesvirus entry mediator (HVEM) (TNFRSF14) binds the canonical TNF-related ligands, lymphotoxin-α (LT-α) and LIGHT; however, the distinguishing feature of HVEM is engagement of members of the immunoglobulin superfamily, B and T lymphocyte attenuator (BTLA) and CD160. The ability of HVEM to interact with multiple ligands in distinct configurations creates a functionally diverse set of intrinsic and bidirectional signaling pathways. The capacity to bind these different ligands resides in two different topographical regions in the extracellular domain of HVEM. These distinct sites impart the ability of HVEM to activate both pro-inflammatory and inhibitory pathways. With HVEM at the nexus in several signaling pathways, it is not surprising that it plays important roles in the immune system, such as T-cell costimulation, regulation of dendritic cell (DC) homeostasis, autoimmune-mediated inflammatory responses, as well as host defense against pathogens. HVEM may also play significant roles outside the immune system, in the regulation of sensory neuron development and adipocyte metabolism.

BTLA uses a distinct surface to interact with HVEM. BTLA/HVEM pathway plays an important role in the maintenance of immune tolerance and the prevention of autoimmune diseases. BTLA-deficient mice develop rheumatoid arthritis, lymphocytic infiltration, autoimmune hepatitis (AIH)-like diseases, and EAE. HVEM-deficient mice show increased susceptibility to MOG peptide-induced EAE and increased T cell proliferation and cytokine production. Antagonistic HVEM-Ig aggravates autoimmunity in collagen-induced arthritis on DBA1 background mice. Thus, the forced expression of BTLA in activated T cells would be a promising strategy for the treatment of autoimmune diseases.

Regarding tumor immunity, tumor antigen-specific CD8+ T cells appear to persistently express BTLA. It has been reported that CpG vaccination partially down-regulates the expression of BTLA in tumor antigen-specific CD8+ T cells and blocks the BTLA/HVEM-mediated inhibitory signal. Although blocking the BTLA/HVEM pathway seems to be relevant as a means to enhance effector T cell functions, careful attention should be paid to the complexity of HVEM-interacting molecules. CD160, an IgSF inhibitory receptor, also binds HVEM. In addition, LIGHT, a TNF family member, delivers a costimulatory signal upon engagement with HVEM. These multiple pathways make it difficult for us to establish novel therapeutic interventions for malignancies.

The manipulation of BTLA/HVEM pathway may become a promising strategy to treat patients with infections. BTLA is induced during *P. berghei* ANKA infection in mice and anti-BTLA antagonistic mAb significantly reduces the incidence of cerebral malaria caused by the protozoa. Thus, pathogens perturbing the BTLA/HVEM pathway may represent ideal targets for anti-BTLA mAb immunotherapy.

In transplantation, the BTLA/HVEM pathway has a unique role in regulating allogeneic responses. It is noteworthy that BTLA, not PD-1, is strongly induced in alloreactive T cells from mice transplanted with partially MHC-mismatched cardiac allografts. Whereas the allografts survive relatively long term in wild type mice, a rapid rejection is observed in BTLA-deficient mice in this partially mismatched model. This indicates that BTLA and PD-1 may play non-redundant roles in transplantation. BTLA seems to be dominant over PD-1 when immune responses are relatively weak, while PD-1 plays a major role in strong allo-responses. Soluble HVEM-Ig or anti-HVEM mAb can prevent GVHD and allograft rejection. The combination of antagonistic anti-BTLA mAb and CTLA-4-Ig prolongs allograft survival, whereas CTLA-4-Ig or anti-BTLA mAb alone fails to prevent graft rejection.

Successful activation of inhibitory receptor signaling is dependent on the capacity for receptor agonists to engage configurations of the inhibitor receptor in an activated state, similar to the activated receptor-ligand configuration. A receptor agonist in the form of an antibody will engage particular epitopes of inhibitory receptors such as B and T lymphocyte attenuator (BTLA) that can promote this activated configuration leading to enhanced BTLA signaling. The epitope of these antibodies will not overlap with the binding site of the BTLA receptor Herpesvirus entry mediator (HVEM). These antibodies will function to enhance signaling by activating phosphorylation of the BTLA cytoplasmic domain, and recruitment and phosphorylation of associated proteins, including SHP1 and 2, other signaling proteins recruited to the cytoplasmic domain of BTLA as a marker of activation. The activation of inhibitory signaling downstream of BTLA is predicted to negatively regulate normal signal transduction pathways downstream of the T cell receptor in T cells, and of the B cell receptor in B cells. Additionally, BTLA inhibitory signaling negatively regulates IL-7 and type I interferon cytokine signaling in innate cells such as γδ T cells and natural killer (NK) cells.

In one embodiment, the present invention provides a method of treating an autoimmune or inflammatory disorder comprising administering a therapeutic agent that modulates the activity of BTLA to a subject in need thereof, thereby treating the autoimmune or inflammatory disorder. In one aspect, the autoimmune or inflammatory disorder is Addison's disease, amyotrophic lateral sclerosis, Crohn's disease, Cushing's Syndrome, diabetes mellitus type 1, graft versus host disease, Graves' disease, Guillain-Barré syndrome, lupus erythematosus, multiple sclerosis, psoriasis, psoriatic arthritis, rheumatoid arthritis, sarcoidosis, scleroderma, systemic lupus erythematosus, cancer, transplant rejection, or vasculitis. In one aspect, the therapeutic agent is an antibody. In another aspect, the antibody binds to BTLA. In a further aspect, the antibody is an agonistic antibody. In an additional aspect, the antibody binds activated BTLA. In certain aspects, the antibody does not block HVEM binding to BTLA. In one aspect, BTLA signaling is enhanced. In another aspect, the antibody is monoclonal, chimeric, human or humanized. In a specific aspect, the antibody is 6F4. In an additional aspect, an immune response modulator is administered. In certain aspects, the immune response modulator is an eicosanoid, cytokine, prostaglandin, interleukin, chemokine or interferon. In a further aspect, the immune response modulators is CXCL-8, CCL2, CCL3, CCL4, CCL5, CCL11, CXCL10, IL1, IL2, IL3, IL4, IL5, IL6, IL7, IL8, IL9, IL10, IL11, IL12, IL13, IL15, IL17, IL17, INF-α, INF-β, INF-ε, INF-γ, G-CSF, TNF-α, CTLA4, CD20, or CD52. In a specific aspect, the immune response modulator is tocilizumab (Actemra), CDP870 (Cimzia), enteracept (Enbrel), adalimumab (Humira), Kineret, abatacept (Orencia), infliximab (Remicade), rituzimab (Rituxan), golimumab (Simponi), Avonex, Rebif, ReciGen, Plegridy, Betaseron, Copaxone, Novatrone, natalizumab (Tysabri), fingolimod (Gilenya), teriflunomide (Aubagio), BG12, Tecfidera, or alemtuzumab (Campath, Lemtrada).

In another embodiment, the present invention provides a method of decreasing T cell activity comprising contacting a T cell with an agent that modulates the activity of BTLA. In one aspect, the therapeutic agent is an anti-BTLA agonistic antibody. In another aspect, the antibody binds activated BTLA. In an additional aspect, the antibody does not block HVEM binding to BTLA. In a certain aspects, the antibody enhances BTLA signaling. In a specific aspect, the antibody is 6F4.

In an additional embodiment, the present invention provides an antibody that binds activated BTLA. In one aspect, the antibody does not block HVEM binding to BTLA. In another aspect, BTLA signaling is enhanced. In an additional aspect, the binding of the antibody to BTLA results in phosphorylation of the cytoplasmic domain of BTLA. In a further aspect, the binding of the antibody to BTLA recruits SHP1 and SHP2. In a specific aspect, the antibody is 6F4.

In a further embodiment, the present invention provides a pharmaceutical composition comprising an anti-BTLA antibody and a pharmaceutically acceptable carrier.

In one embodiment, the present invention provides a method of screening for a BTLA agonist agent comprising contacting the agent with BTLA; and measuring BTLA activity, wherein an increase in BTLA activity indicates that the agent is a BTLA agonist. In one aspect, the agent is an antibody, antibody fragment or a peptide. In an additional aspect, the antibody is monoclonal, chimeric, human or humanized. In a further aspect, the antibody binds to the same epitope as clone 6F4.

The examples below describe a monoclonal antibody directed against human BTLA (antibody clone 6F4) that enhances interactions with the BTLA receptor HVEM in a titrated fashion. The binding of the natural ligand, LIGHT in soluble form enhances HVEM binding to BTLA, thus 6F4 mimics the natural ligand. The 6F4 antibody does not alter BTLA interactions with a viral paralog of HVEM expressed in Cytomegalovirus (orf UL144). This antibody shows reactivity exclusively to BTLA, and the epitope of this antibody does not overlap with the epitopes of antagonist (HVEM blocking) antibodies (clone J168 and clone MIH128). Anti BTLA 6F4 fulfills the prediction of an inhibitory receptor agonist. This antibody fixes the configuration of BTLA in an active state, allowing for increased HVEM binding and subsequent BTLA signaling. This antibody and others like it will inhibit lymphocyte activation, and further, this class of antibodies will be of potential therapeutic benefit in immune mediated pathologies.

The invention in all its aspects is illustrated further in the following Examples. The Examples do not, however, limit the scope of the invention, which is defined by the appended claims.

EXAMPLES

Example 1

BTLA Agonist Antibodies

The anti-human BTLA monoclonal antibody clone 6F4 was produced from a Sprague-Dawley rat immunized with huBTLA:huIgG recombinant fusion protein produced in 293T cells. Spleen cells from the immunized rat were fused with SP2/0-Ag14 myeloma partner cells following a classic PEG-fusion protocol and selected in HAT medium. The resulting hybridoma clones were screened by ELISA against huBTLA:huIgG and purified huIgG to identify those specific for huBTLA. A secondary screen was performed by binding to Beg+/+MEF cells expressing huBTLA and analyzing by flow cytometry compared to the non-BTLA expressing parental cells. Clone 6F4 was identified as reactive to huBTLA, further subcloned and expanded for purification of the antibody by protein G affinity chromatography. The isotype of 6F4 was determined using Rat Immunoglobulin Isotyping Kit (BD).

The amino acid sequence was determined for the 6F4 antibody. Tryptic peptide masses were used to search database for identification of the protein sequence of the 6F4 antibody constant region. Both light (FIG. 3A, SEQ ID NO: 1) and heavy (FIG. 3B, SEQ ID NO: 2) chain constant regions were identified. After identification of most tryptic peptides, MS/MS was used to determine remaining peptide sequences, subsequently identified by BLAST search. Peptides containing CDRs were collected for N-terminal sequencing for confirmation.

Example 2

Characterization of Anti-BTLA Monoclonal Antibodies

Figure 1B:
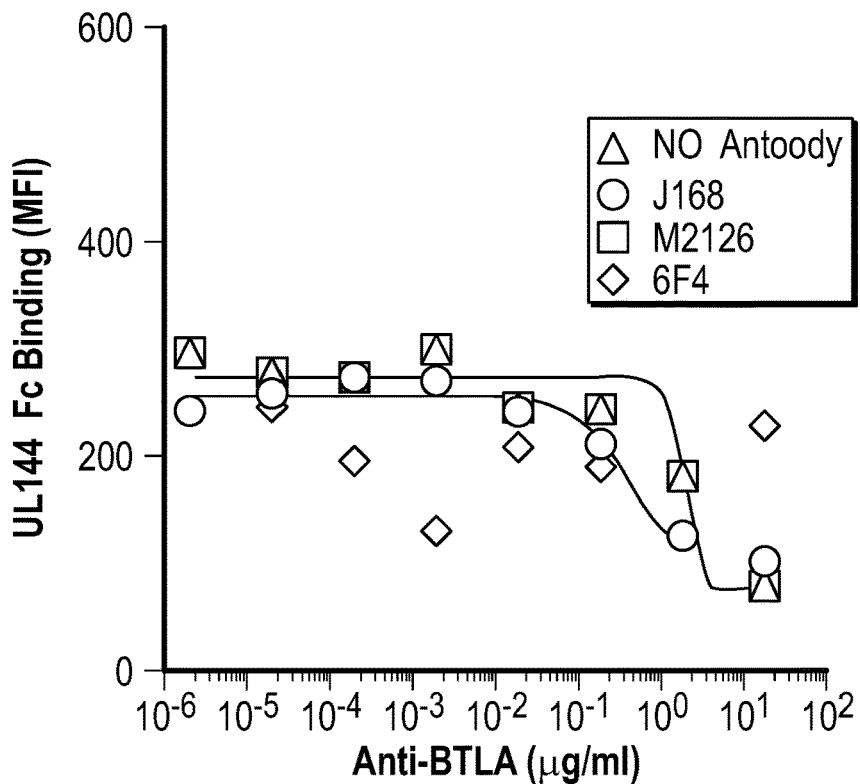
Figure 1C:
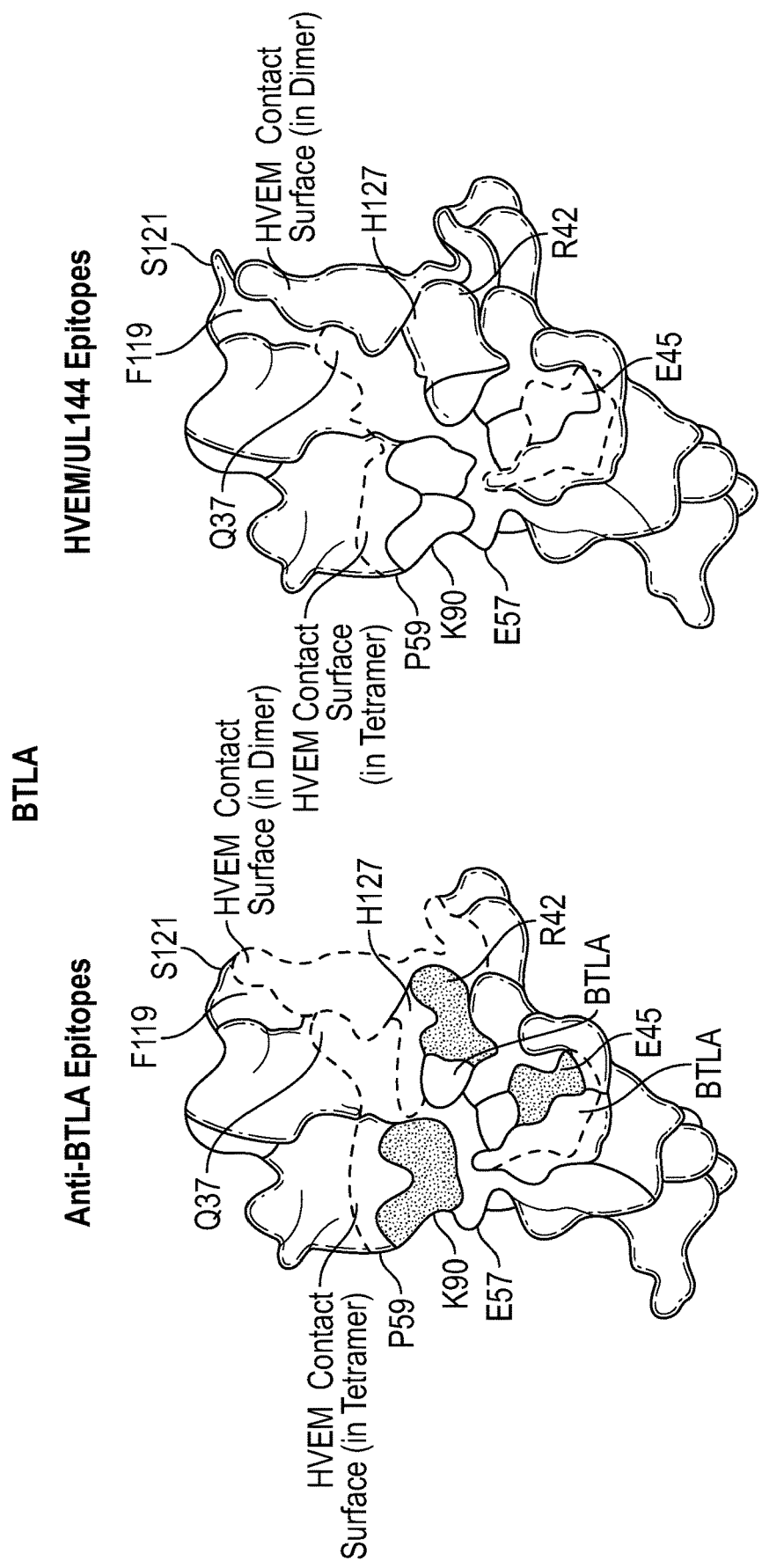

BJAB cells transduced with BTLA were incubated with the indicated concentrations of anti-BTLA antibodies prior to staining with 20 ug/ml of HVEM-Fc or human CMV UL144-Fc (FIGS. 1 A and B.). Graphs show curves of antibody blockade of HVEM and UL144-Fc cell binding. Two images of BTLA are shown (FIG. 1C). Binding surfaces of HVEM and a BTLA dimer are predicted using the structure of HVEM and BTLA. In the left image specific residues indicate a requirement for antibody binding: Glu45, Glu57, Pro59 (required for MIH26 binding), Arg42 (required for J168 binding). In the right image specific residues indicate the HVEM/UL144 binding epitope: Gln37, Arg42, Pro59, His127 (required for HVEM/UL144 binding), Glu45, Glu57, Phe119, Ser121 (not required for HVEM/UL144 binding).

Example 3

Figure 2B:
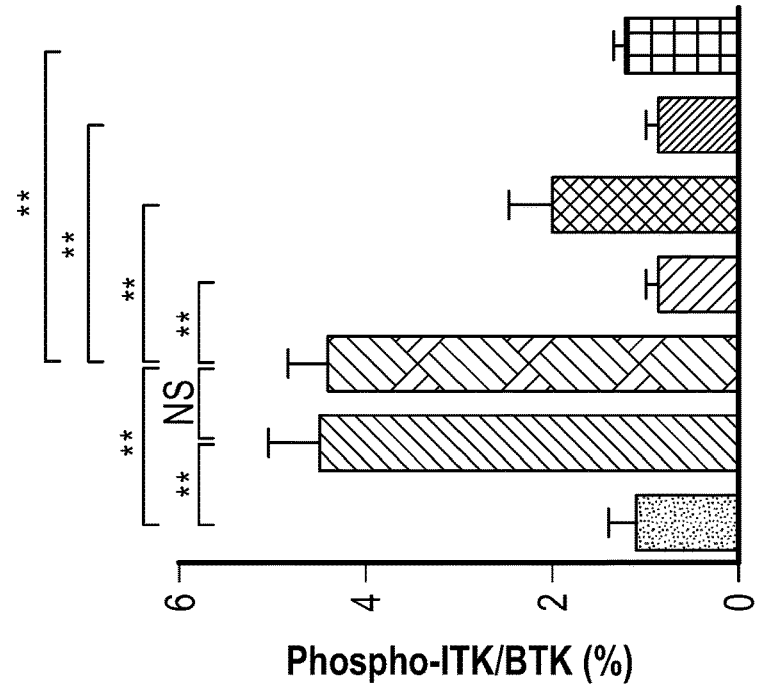
FIGS. 2A-2F show similar BTLA agonism among diverse pathogen associated and de novo bioengineered HVEM muteins. JTAg cells transduced with the indicated HVEM ligands were cultured with microspheres coupled to anti-CD3 with or without Fc proteins prior to intracellular staining for (A) phospho-ZAP70/Syk, (B) phospho-BTK/ITK, (C) phospho-PLCγ1, (D) phospho-ERK1/2, (E) phospho-tyrosine and (F) phospho-ERK1/2.
Figure 2A:
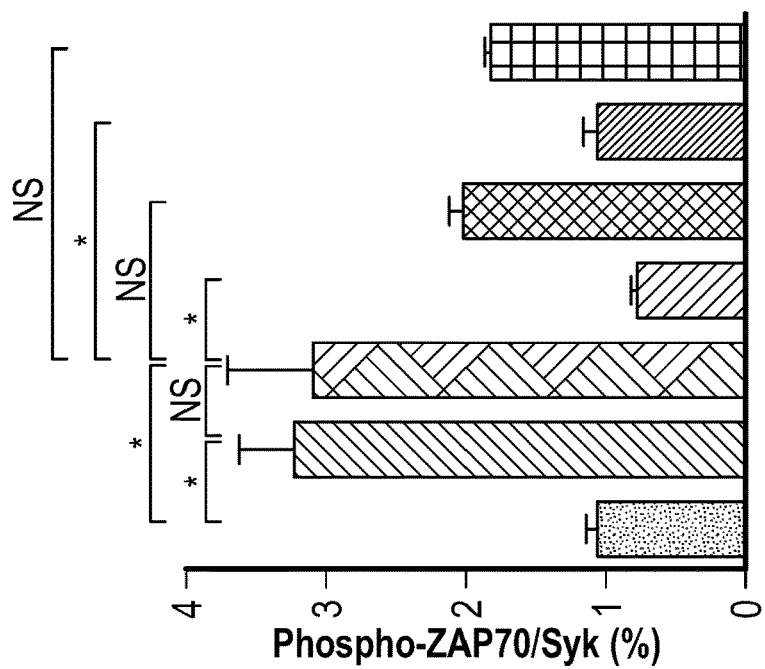
Figure 2D:
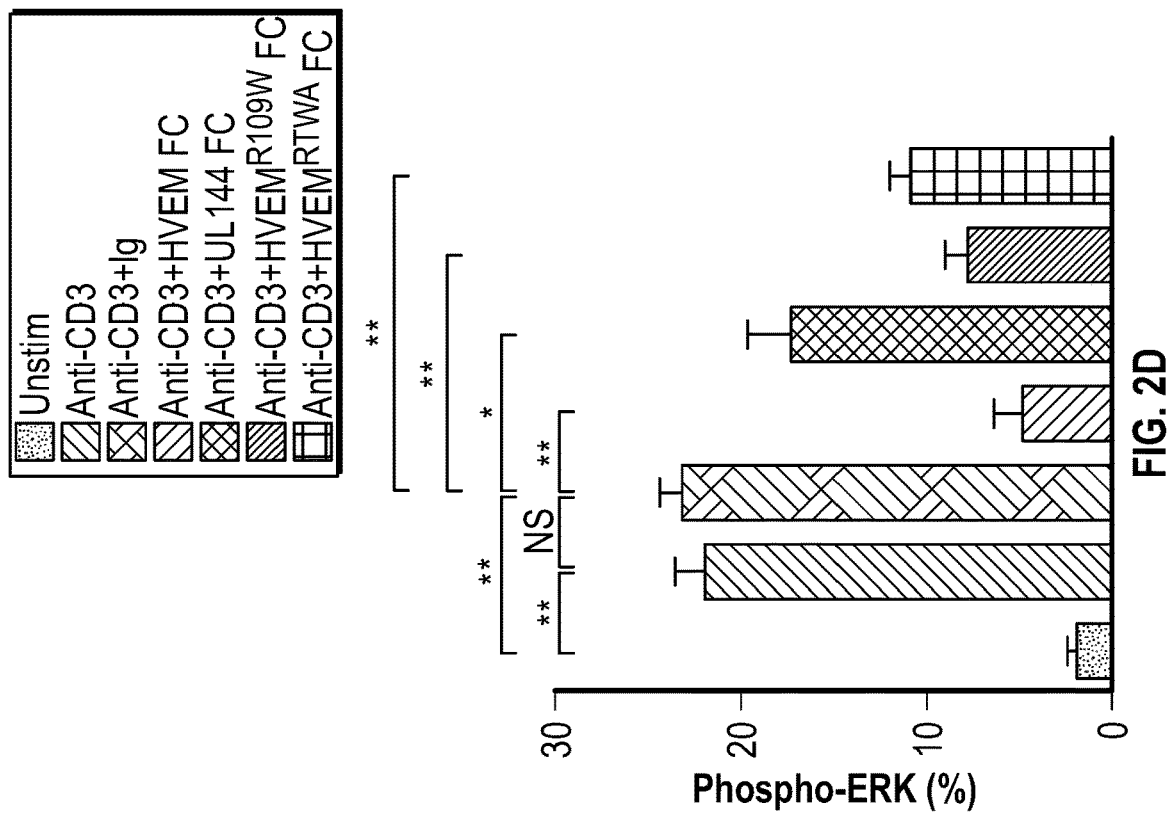
Figure 2C:
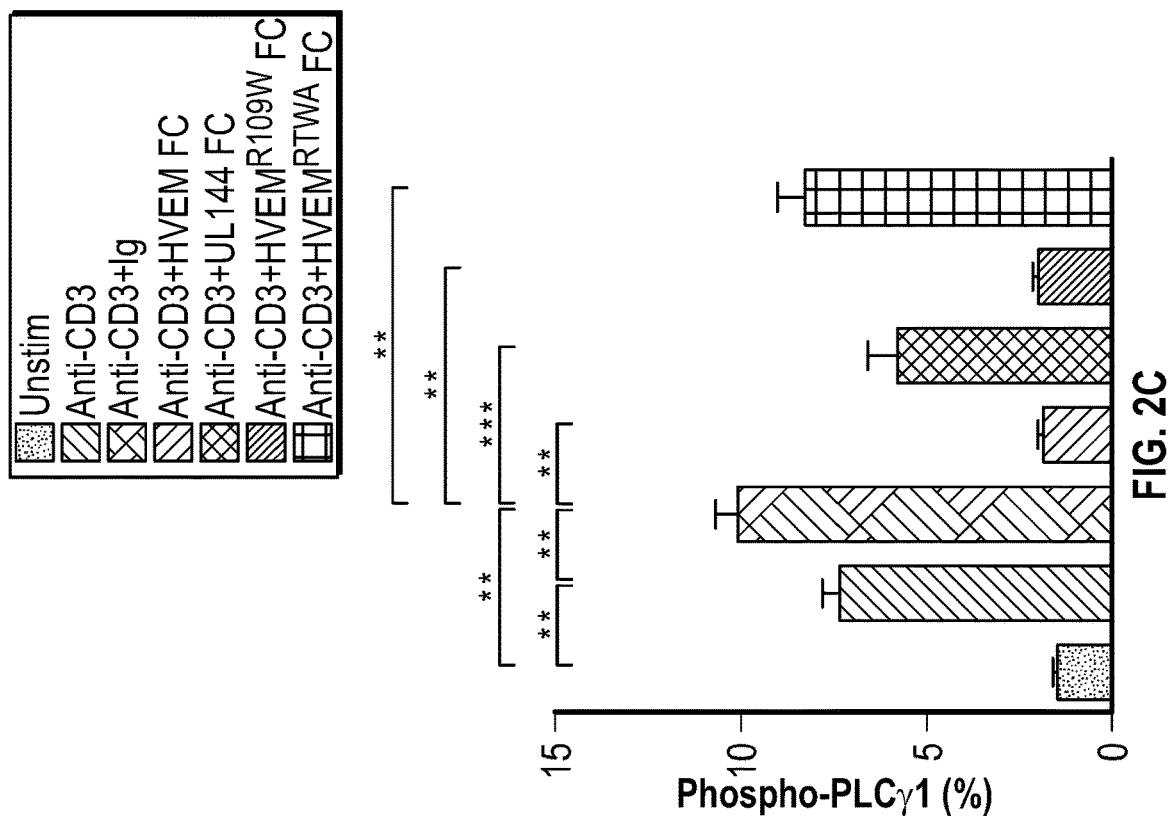
Figure 2E:
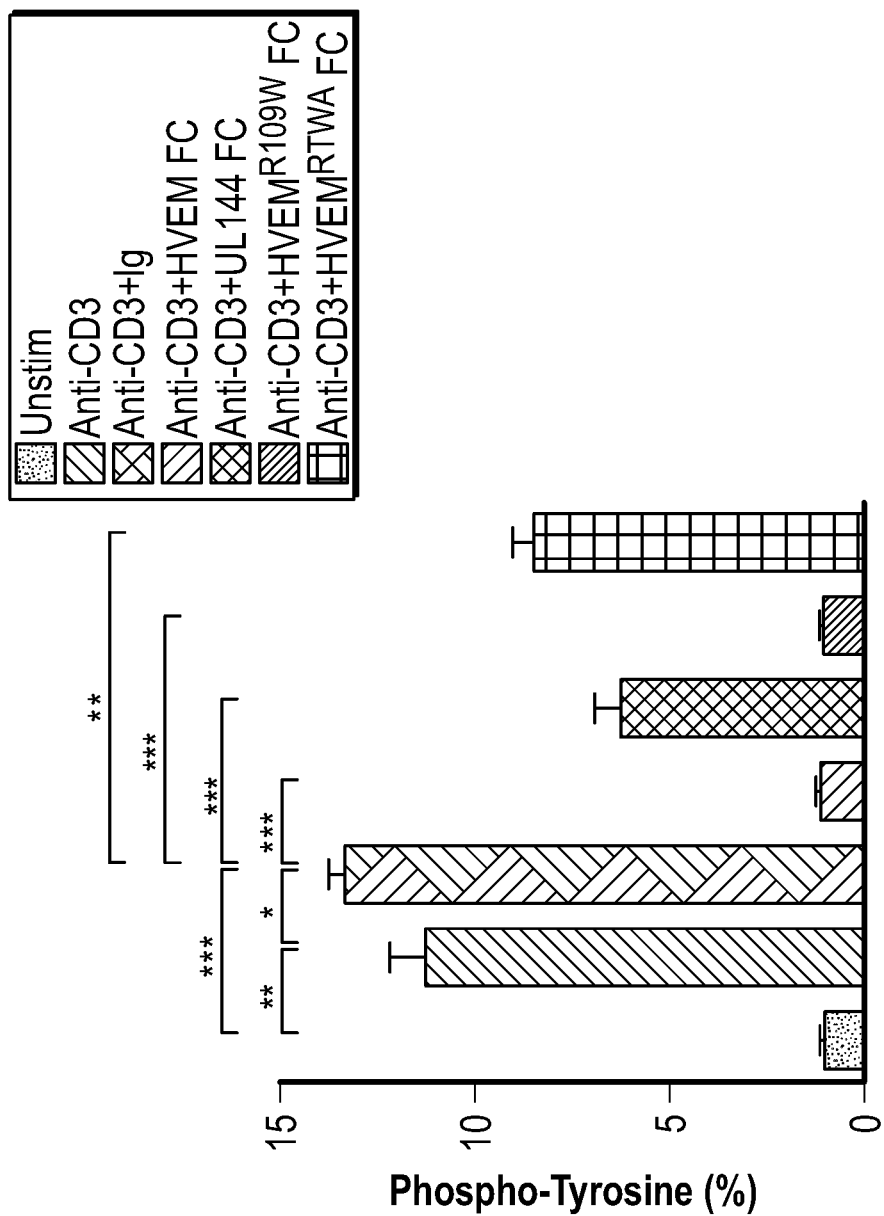
Figure 2F:
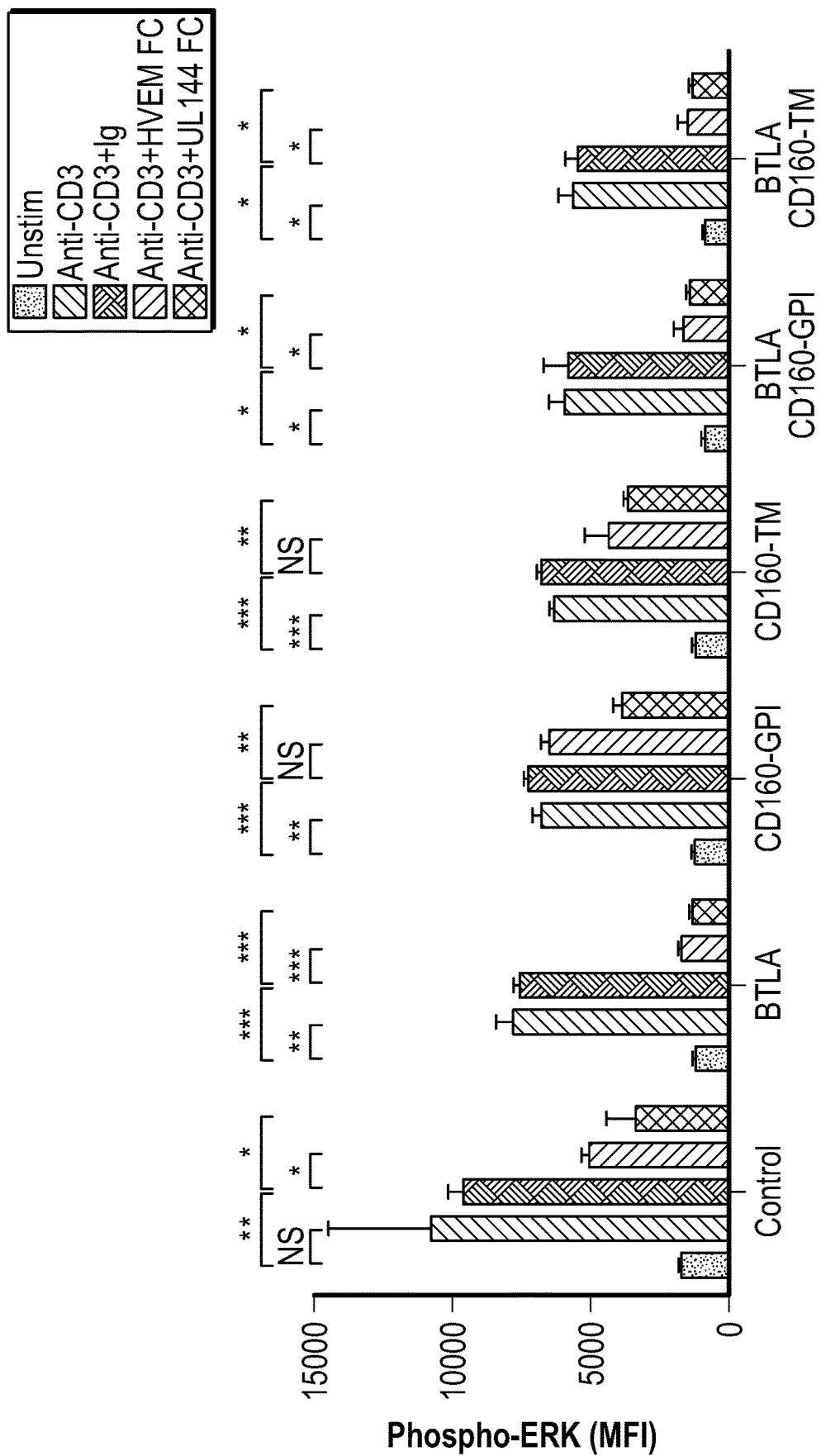

BTLA Agonism Among Diverse Pathogen-Associated and De Novo Bioengineered HVEM Muteins BTLA agonism was examined using the HVEM mutein, UL144, and lymphoma mutants. The results showed decreased phosphorylation of proteins downstream of TCR activation, including ITK/BTK, PLCg1, ZAP70/Syk, ERK, as well as total tyrosine phosphorylation. JTAg cells transduced with the indicated HVEM ligands were cultured with microspheres coupled to anti-CD3 with or without Fc proteins for 5 minutes prior to intracellular staining for phospho-ZAP70/Syk (Y319/Y352) (FIG. 2A), phospho-BTK/ITK (Y551/Y511) (FIG. 2B), phospho-PLCγ1 (Y783) (FIG. 2C), phospho-ERK1/2 (T202/Y204) (FIGS. 2D and F), and phospho-tyrosine (FIG. 2E). Graphs show the % positive of stained cells, and in (F) the MFI of stained cells (FIGS. 2A-F). (mean±SEM representative of three experiments). *, $p<0.05$; , $p<0.01$; *, $p<0.001$. It was concluded from these experiments that the mechanism of BTLA inhibition of T cell activation as modeled by BTLA engagement with HVEM, the HVEM mutein, UL144, or the lymphoma mutants is inactivation of signaling proteins immediately triggered by the T cell receptor including ITK, PLCg1, ZAP70, as well as downstream signaling proteins such as ERK.

Example 4

BTLA Regulates Severity of EAE

Figure 4A:
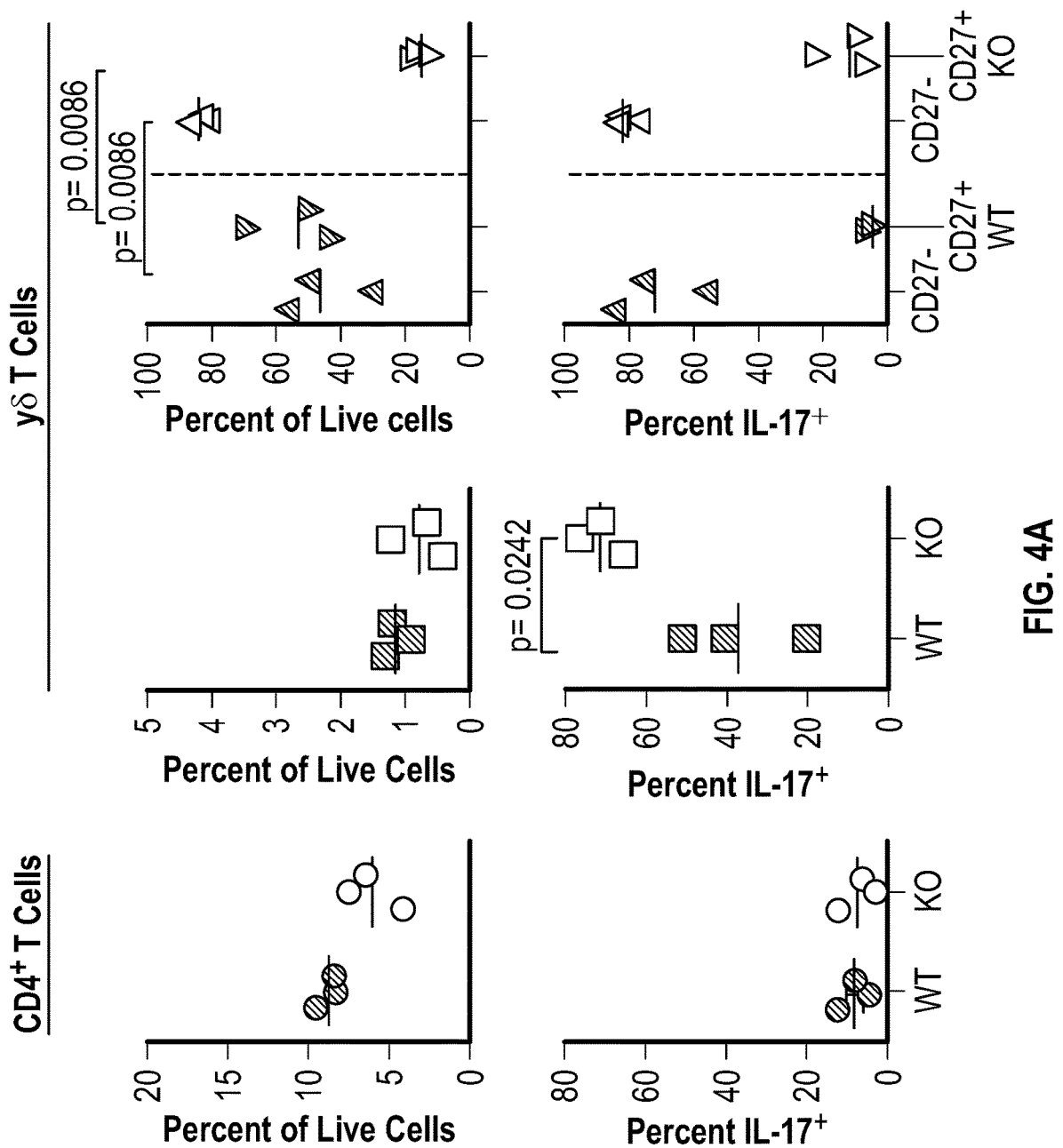
FIGS. 4A-4B show that BTLA regulates the severity of EAE. (A) Central nervous system infiltrating lymphocytes were analyzed for the presence of CD4+ and gamma delta T cells, and IL-17 production after wild type and BTLA deficient animals were immunized with low dose MOG peptide. (B) Average EAE scores of MOG immunized animals showing reduction of disease severity in anti-BTLA treated animals.
Figure 4B:
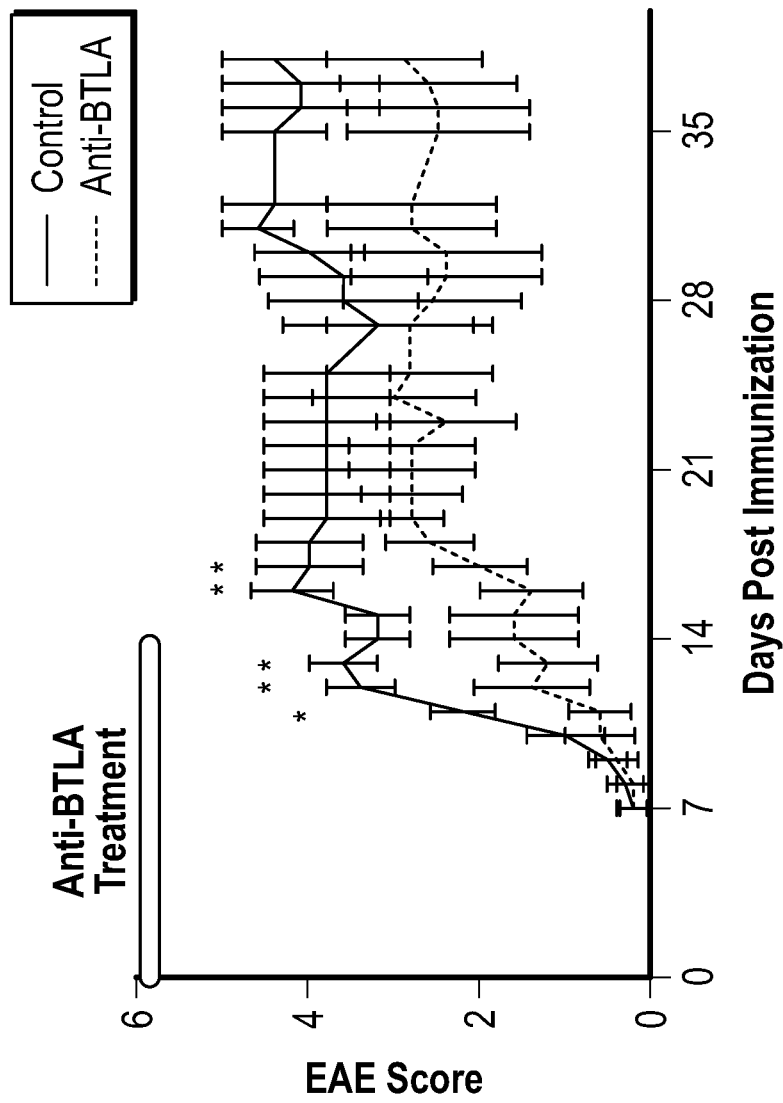

Wild-type and BTLA-deficient animals were immunized with low dose MOG peptide (50 μg in CFA) and central nervous system infiltrating lymphocytes were analyzed for the presence of CD4+ and gamma delta T cells, and IL-17 production (FIG. 4A). Wild-type animals immunized with MOG peptide (50 µg in CFA) were treated with anti-BTLA (clone 6A6) biweekly for two weeks and monitored for symptoms relating to EAE. FIG. 4B shows average scores of immunized animals showing reduction of disease severity in anti-BTLA treated animals (FIG. 4B). It was concluded that BTLA deficiency selectively controls the activation of gamma delta T cells during neuroinflammation, and that anti-BTLA antibody treatment can limit the severity of neuroinflammation, in part through control of gamma delta T cell activation.

Although the invention has been described with reference to the above examples, it will be understood that modifications and variations are encompassed within the spirit and scope of the invention. Accordingly, the invention is limited only by the following claims.

What is claimed is:

1. A method of treating an autoimmune or inflammatory disorder in a subject comprising administering to a subject in need thereof a BTLA agonistic antibody, wherein the antibody binds to activated BTLA and does not block HVEM binding to BTLA and comprises all three complementarity-determining regions (CDRs) of SEQ ID NO: 1, and all three CDRs of SEQ ID NO: 2; wherein the autoimmune or inflammatory disorder is selected from the group consisting of: Addison's disease, amyotrophic lateral sclerosis, Crohn's disease, Cushing's Syndrome, diabetes mellitus type 1, graft versus host disease, Graves' disease, Guillain-Barre syndrome, lupus erythematosus, multiple sclerosis, psoriasis, psoriatic arthritis, rheumatoid arthritis, sarcoidosis, scleroderma, systemic lupus erythematosus, transplant rejection, and vasculitis.

2. The method of claim 1, wherein BTLA signaling is enhanced.

3. The method of claim 1, wherein the antibody is monoclonal, chimeric, human, or humanized or a binding fragment thereof.

4. The method of claim 1, further comprising administering an immune response modulator, wherein the immune response modulator is selected from the group consisting of: tocilizumab (Actemra), CDP870 (Cimzia), etanercept (Enbrel), adalimumab (Humira), Kineret, abatacept (Orencia), infliximab (Remicade), rituximab (Rituxan), golimumab (Simponi), Avonex, Rebif, ReciGen, Plegridy, Betaseron, Copaxone, Novatrone, natalizumab (Tysabri), fingolimod (Gilenya), teriflunomide (Aubagio), BG12, Tecfidera, and alemtuzumab (Campath, Lemtrada).

5. A method of decreasing T cell activity comprising contacting a T cell with a BTLA agonistic antibody and an immune response modulator, wherein the antibody binds activated BTLA and does not block HVEM binding to BTLA and comprises all three complementarity-determining regions (CDRs) of SEQ ID NO: 1, and all three CDRs of SEQ ID NO: 2, wherein the immune response modulator is selected from the group consisting of prostaglandins and chemokines, and wherein the immune response modulator decreases T cell activity.

6. The method of claim 5, wherein BTLA signaling is enhanced.

7. The method of claim 5, wherein the contacting is in vivo or ex vivo.

* * * * *

UNITED STATES PATENT AND TRADEMARK OFFICE
CERTIFICATE OF CORRECTION

Page 1 of 1

PATENT NO. : 11,352,428 B2
APPLICATION NO. : 15/570013
DATED : June 7, 2022
INVENTOR(S) : Carl F. Ware, John Sedy and Paula Norris It is certified that error appears in the above-identified patent and that said Letters Patent is hereby corrected as shown below:

In the Specification

In Column 1, Lines 17 through 20, please replace:
"This invention was made in part with government support under Grant No. R37A1033068 awarded by the National Institutes of Health. The United States government has certain rights in this invention."

With:
"This invention was made with government support under R37 AI033068 awarded by the National Institutes of Health. The government has certain rights in the invention."

Signed and Sealed this
Second Day of August, 2022

Katherine Kelly Vidal
*Director of the United States Patent and Trademark Office*

SEQUENCE LISTING

```
<160> NUMBER OF SEQ ID NOS: 2

<210> SEQ ID NO 1
<211> LENGTH: 214
<212> TYPE: PRT
<213> ORGANISM: Mus musculus
<220> FEATURE:
<221> NAME/KEY: misc_feature
<223> OTHER INFORMATION: 6F4 Antibody  Light chain

<400> SEQUENCE: 1

Asp Ile Gln Met Thr Gln Ser Pro Ser Val Leu Ser Val Ser Val Gly
1               5                   10                  15

Asp Arg Val Thr Leu Asn Cys Lys Ala Ser His Asn Ile Lys Asn Tyr
            20                  25                  30

Leu Asn Trp Tyr Gln Gln Lys Leu Gly Glu Ala Pro Lys Leu Leu Ile
        35                  40                  45

Tyr Asp Thr Val Asn Leu Gln Thr Gly Ile Pro Ser Arg Phe Ser Gly
    50                  55                  60

Ser Gly Ser Gly Thr Asp Phe Thr Val Thr Ile Ser Ser Leu Gln Pro
65                  70                  75                  80

Glu Asp Val Ala Thr Tyr Phe Cys Phe Gln Tyr His Ser Trp Pro Tyr
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Met Glu Gln Leu Thr Ser Gly
        115                 120                 125

Gly Ala Thr Val Val Cys Phe Val Asn Asn Phe Tyr Pro Arg Asp Ile
    130                 135                 140

Ser Val Lys Trp Lys Ile Asp Gly Ser Glu Gln Arg Asp Gly Val Leu
145                 150                 155                 160

Asp Ser Val Thr Asp Gln Asp Ser Lys Asp Ser Thr Tyr Ser Met Ser
                165                 170                 175

Ser Thr Leu Ser Leu Thr Lys Val Glu Tyr Glu Arg His Asn Leu Tyr
            180                 185                 190

Thr Cys Glu Val Val His Lys Thr Ser Ser Ser Pro Val Val Lys Ser
        195                 200                 205

Phe Asn Arg Asn Glu Cys
    210

<210> SEQ ID NO 2
<211> LENGTH: 452
<212> TYPE: PRT
<213> ORGANISM: Mus musculus
<220> FEATURE:
<221> NAME/KEY: misc_feature
<223> OTHER INFORMATION: 6F4 Antibody heavy chain

<400> SEQUENCE: 2

Glu Val Gln Ile Leu Glu Thr Gly Gly Gly Leu Val Lys Pro Gly Gly
```

```
1               5                   10                  15
Ser Leu Arg Leu Ser Cys Ala Thr Ser Gly Phe Asn Phe Asn Asp Tyr
            20                  25                  30

Phe Val Asn Trp Val Arg Gln Ala Pro Gly Lys Gly Leu Gln Trp Val
            35                  40                  45

Ala Gln Ile Arg Asn Lys Asn Tyr Asn Pro Ala Thr Tyr Tyr Ala Glu
50                  55                  60

Ser Leu Glu Gly Arg Val Thr Ile Ser Arg Asp Asp Ser Lys Ser Ser
65                  70                  75                  80

Val Tyr Leu Gln Val Ser Ser Val Arg Ala Glu Asp Thr Ala Ile Tyr
            85                  90                  95

Tyr Cys Ser Pro Ile Ser Ser Tyr Tyr His Asp Gly Ser Leu His Tyr
            100                 105                 110

Ser Asp Tyr Trp Gly Gln Gly Val Met Val Thr Val Ser Ser Ala Glu
            115                 120                 125

Thr Thr Ala Pro Ser Val Tyr Pro Leu Ala Pro Gly Thr Ala Leu Lys
            130                 135                 140

Ser Asn Ser Met Val Thr Leu Gly Cys Leu Val Lys Gly Tyr Phe Pro
145                 150                 155                 160

Glu Pro Val Thr Val Thr Trp Asn Ser Gly Ala Leu Ser Ser Gly Val
            165                 170                 175

His Thr Phe Pro Ala Val Leu Gln Ser Gly Leu Tyr Thr Leu Thr Ser
            180                 185                 190

Ser Val Thr Val Pro Ser Ser Thr Trp Pro Ser Gln Thr Val Thr Cys
            195                 200                 205

Asn Val Ala His Pro Ala Ser Ser Thr Lys Val Asp Lys Lys Ile Val
            210                 215                 220

Pro Arg Asn Cys Gly Gly Asp Cys Lys Pro Cys Ile Cys Thr Gly Ser
225                 230                 235                 240

Glu Val Ser Ser Val Phe Ile Phe Pro Pro Lys Pro Lys Asp Val Leu
            245                 250                 255

Thr Ile Thr Leu Thr Pro Lys Val Thr Cys Val Val Val Asp Ile Ser
            260                 265                 270

Gln Asp Asp Pro Glu Val His Phe Ser Trp Phe Val Asp Asp Val Glu
            275                 280                 285

Val His Thr Ala Gln Thr Arg Pro Pro Glu Glu Gln Phe Asn Ser Thr
            290                 295                 300

Phe Arg Ser Val Ser Glu Leu Pro Ile Leu His Gln Asp Trp Leu Asn
305                 310                 315                 320

Gly Arg Thr Phe Arg Cys Lys Val Thr Ser Ala Ala Phe Pro Ser Pro
            325                 330                 335

Ile Glu Lys Thr Ile Ser Lys Pro Glu Gly Arg Thr Gln Val Pro His
            340                 345                 350

Val Tyr Thr Met Ser Pro Thr Lys Glu Glu Met Leu Gln Asn Glu Val
            355                 360                 365

Ser Ile Thr Cys Met Val Lys Gly Phe Tyr Pro Pro Asp Ile Tyr Val
            370                 375                 380

Glu Trp Gln Met Asn Gly Gln Pro Gln Glu Asn Tyr Lys Asn Thr Pro
385                 390                 395                 400

Pro Thr Met Asp Thr Asp Gly Ser Tyr Phe Leu Tyr Ser Lys Leu Asn
            405                 410                 415

Val Lys Lys Glu Lys Trp Gln Gln Gly Asn Thr Phe Thr Cys Ser Val
            420                 425                 430
```

```
Leu His Glu Gly Leu His Asn His His Thr Glu Lys Ser Leu Ser His
        435                 440                 445
Ser Pro Gly Lys
    450
```